(12) United States Patent
Kim et al.

(10) Patent No.: US 8,386,039 B2
(45) Date of Patent: *Feb. 26, 2013

(54) RHYTHM DISCRIMINATION OF SUDDEN ONSET AND ONE-TO-ONE TACHYARRHYTHMIA

(75) Inventors: Jaeho Kim, Redmond, WA (US); Joseph M. Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 147 days.

This patent is subject to a terminal disclaimer.

(21) Appl. No.: 12/825,618

(22) Filed: Jun. 29, 2010

(65) Prior Publication Data

US 2010/0262030 A1 Oct. 14, 2010

Related U.S. Application Data

(62) Division of application No. 11/276,213, filed on Feb. 17, 2006, now Pat. No. 7,756,578.

(51) Int. Cl.
*A61B 5/0464* (2006.01)
(52) U.S. Cl. .......................................... 607/14; 600/518
(58) Field of Classification Search .................. 607/14; 600/518
See application file for complete search history.

(56) References Cited

U.S. PATENT DOCUMENTS

| | | | |
|---|---|---|---|
| 5,063,928 A | 11/1991 | Grevis et al. | |
| 5,327,900 A | 7/1994 | Mason et al. | |
| 5,379,776 A | 1/1995 | Murphy et al. | |
| 5,462,060 A | 10/1995 | Jacobson et al. | |
| 5,891,170 A | 4/1999 | Nitzsche et al. | |
| 5,978,707 A | 11/1999 | Krig et al. | |
| 6,076,014 A | 6/2000 | Alt | |
| 6,522,917 B1 | 2/2003 | Hsu et al. | |
| 6,611,713 B2 | 8/2003 | Schauerte | |
| 6,636,764 B1 | 10/2003 | Fain et al. | |
| 7,328,063 B2 | 2/2008 | Zhang et al. | |
| 7,818,056 B2 | 10/2010 | Kim et al. | |
| 8,032,217 B2 | 10/2011 | Kim et al. | |
| 8,145,301 B2 | 3/2012 | Kim et al. | |
| 2003/0060849 A1 | 3/2003 | Hsu | |
| 2003/0074026 A1 | 4/2003 | Thompson et al. | |
| 2004/0088013 A1 | 5/2004 | Stadler et al. | |
| 2004/0093035 A1 | 5/2004 | Schwartz et al. | |
| 2005/0137485 A1* | 6/2005 | Cao et al. | 600/510 |
| 2006/0217621 A1* | 9/2006 | Kim et al. | 600/509 |
| 2007/0135848 A1 | 6/2007 | Kim et al. | |
| 2010/0168597 A1 | 7/2010 | Kim et al. | |
| 2011/0021934 A1 | 1/2011 | Kim et al. | |

OTHER PUBLICATIONS

"U.S. Appl. No. 11/276,213, Examiner Interview Summary mailed Jul. 27, 2009", 4 pgs.
"U.S. Appl. No. 11/276,213, Final Office Action Mailed Nov. 10, 2009", 8 pgs.
"U.S. Appl. No. 11/276,213, Non Final Office Action mailed May 6, 2009", 10 pgs.

(Continued)

*Primary Examiner* — Eric D. Bertram
(74) *Attorney, Agent, or Firm* — Schwegman Lundberg & Woessner, P.A.

(57) ABSTRACT

This document discusses, among other things, systems and methods to discriminate between a ventricular tachyarrhythmia (VT) and a supraventricular tachyarrhythmia (SVT), such as upon detecting sudden onset and one-to-one tachycardia. In certain examples, a detected tachyarrhythmia is analyzed to determine whether it is sudden onset and 1:1. If so, a first fast beat is identified. One or more ventricular intervals in close proximity to the first fast beat are analyzed to determine an initial classification of either VT or SVT. The initial classification is used to adjust a morphological feature correlation coefficient (FCC) threshold. A morphology analysis is performed with the adjusted FCC threshold value to yield a secondary classification.

16 Claims, 7 Drawing Sheets

OTHER PUBLICATIONS

"U.S. Appl. No. 11/276,213, Notice of Allowance mailed Mar. 2, 2010", 4 pgs.

"U.S. Appl. No. 11/276,213, Response filed Jan. 21, 2010 to Final Office Action mailed Nov. 10, 2009", 6 pgs.

"U.S. Appl. No. 11/276,213, Response filed Mar. 25, 2009 to Restriction Requirement mailed Feb. 27, 2009", 12 pgs.

"U.S. Appl. No. 11/276,213, Response filed Aug. 6, 2009 to Non Final Office Action mailed May 6, 2009", 11 pgs.

"U.S. Appl. No. 11/276,213, Restriction Requirement mailed Feb. 27, 2009", 7 pgs.

"U.S. Appl. No. 11/301,716, Non-Final Office Action mailed Apr. 16, 2009", 18 pgs.

"U.S. Appl. No. 11/301,716, Non-Final Office Action mailed Sep. 16, 2008", 18 pgs.

"U.S. Appl. No. 11/301,716, Notice of Allowance mailed Dec. 4, 2009", 10 pgs.

"U.S. Appl. No. 11/301,716, Response filed Jul. 16, 2009 to Non Final Office Action mailed Apr. 16, 2009", 16 pgs.

"U.S. Appl. No. 11/301,716, Response filed Dec. 16, 2008 to Non-Final Office Action mailed Sep. 16, 2008", 21 pgs.

Bansch, D., et al., "The 1+1 trial: a prospective trial of a dual- versus a single-chamber implantable defibrillator in patients with slow ventricular tachycardias.", *Circulation*, 110(9), (Aug. 31, 2004), 1022-9.

Chiang, et al., "Median Filtering as a Sudden Onset Criterion to Separate Sinus Tachycardia from Ventricular Tachycardia", *Proceedings of Computers in Cardiology*, (1992), 379-382.

"U.S. Appl. No. 11/301,716, Examiner Interview Summary filed Jan. 4, 2010", 1 pg.

"U.S. Appl. No. 11/301,716, Examiner Interview Summary mailed Nov. 25, 2008", 4 pgs.

"U.S. Appl. No. 12/723,805, Examiner Interview Summary mailed Jan. 19, 2011", 4 pgs.

"U.S. Appl. No. 12/723,805, Non-Final Office Action mailed Oct. 14, 2010", 12 pgs.

"U.S. Appl. No. 12/723,805, Notice of Allowance mailed Jun. 3, 2011", 10 pgs.

"U.S. Appl. No. 12/723,805, Response filed Jan. 13, 2011 to Non-Final Office Action mailed Oct. 14, 2010", 13 pgs.

"U.S. Appl. No. 12/895,151, Examiner Interview Summary mailed Jul. 14, 2011", 3 pgs.

"U.S. Appl. No. 12/895,151, Final Office Action mailed Aug. 29, 2011", 7 pgs.

"U.S. Appl. No. 12/895,151, Non-Final Office Action mailed Mar. 23, 2011", 8 pgs.

"U.S. Appl. No. 12/895,151, Notice of Allowance mailed Nov. 25, 2011", 7 pgs.

"U.S. Appl. No. 12/895,151, Response filed Jun. 22, 2011 to Non-Final Office Action mailed Mar. 23, 2011", 13 pgs.

"U.S. Appl. No. 12/895,151, Response filed Aug. 31, 2011 to Final Office Action mailed Aug. 29, 2011", 2 pgs.

* cited by examiner

RHYTHM DISCRIMINATION OF SUDDEN ONSET AND ONE-TO-ONE TACHYARRHYTHMIA

CROSS-REFERENCE TO RELATED APPLICATIONS

This application is a divisional of U.S. application Ser. No. 11/276,213, now issued as U.S. Pat. No. 7,756,578, filed Feb. 17, 2006, which is hereby incorporated by reference in its entirety.

This application is related to co-pending, commonly assigned, U.S. patent application Ser. No. 11/301,716, now issued as U.S. Pat. No. 7,702,384, entitled "ZONELESS TACHYARRHYTHMIA DETECTION WITH REAL-TIME RHYTHM MONITORING," filed on Dec. 13, 2005, which is hereby incorporated herein by reference in its entirety.

TECHNICAL FIELD

The field generally relates to implantable medical devices and, in particular, but not by way of limitation, to systems and methods for tachyarrhythmia detection or discrimination.

BACKGROUND

Implantable medical devices (IMDs) are devices designed to be implanted into a patient. Some examples of these devices include cardiac function management (CFM) devices. CFMs include implantable pacemakers, implantable cardioverter defibrillators (ICDs), cardiac resynchronization therapy devices, and devices that include a combination of such capabilities. The devices are typically used to treat patients using electrical therapy and to aid a physician or caregiver in patient diagnosis through internal monitoring of a patient's condition. The devices may include electrical leads or other electrodes in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. In CFM devices, these events typically include depolarizations indicative of heart chamber contractions or repolarizations indicative of heart chamber expansions. By monitoring cardiac signals indicative of expansions or contractions, some IMDs are able to detect a tachyarrhythmia. Such IMDs typically provide therapy for tachyarrhythmia, such as high energy shock therapy or anti-tachycardia pacing (ATP). Tachyarrhythmia includes abnormally rapid heart rate, or tachycardia, including ventricular tachycardia (VT) and supraventricular tachycardia (SVT).

SUMMARY

Typically, CFMs discriminate between or classify tachyarrhythmias based on either a rate or interval-based method or a morphology-based method. The rate or interval based method typically compares heart rate (or, inversely, the time interval between successive depolarizations) to various rate zones to discriminate between or classify tachyarrhythmias. The morphology-based method typically compares the shape of a cardiac depolarization to a template morphology to discriminate between or classify tachyarrhythmias. The comparison results in a correlation value (e.g., a feature correlation coefficient (FCC)) that indicates a degree of similarity between the shape of a depolarization being examined and the shape of the template to which it is compared. The FCC can be compared to an FCC threshold value to classify the tachyarrhythmia beat as SVT or VT. In an illustrative example, a depolarization being examined is compared to a normal sinus rhythm (NSR) template and, if the comparison of the FCC to the FCC threshold indicates that the depolarization being examined is well-correlated to such an NSR template, then the depolarization being examined is classified as an SVT instead of a VT. The morphology-based method typically operates using cardiac signals sensed via a "shock channel" that includes at least one large surface area "shock" electrode. The rate or interval-based method typically operates using cardiac signals sensed via a "rate channel" that uses smaller surface area "pacing electrodes" such as ring or tip electrodes. However, the morphology-based method can also make use of the rate channel, such as to synchronize the timing of the shock channel depolarization with the template depolarization.

However, particularly when the tachyarrhythmia exhibits a sudden onset with a 1:1 atrial-to-ventricular rate, these individual methods can be inaccurate, which may result in inappropriate therapies. Typically, a rate or interval-based rhythm discriminator classifies a tachyarrhythmia as a supraventricular tachyarrhythmia (SVT) when: (1) the heart rate or ventricular rate is unstable, or (2) the tachyarrhythmia exhibits a gradual onset and is stable (stability can be determined from the beat-to-beat variability in heart rate or depolarization intervals). However, the rate or interval-based tachyarrhythmia classification decision can be indeterminate when the rhythm is sudden onset and 1:1 because the rhythm could be SVT with anterograde conduction or VT with retrograde conduction.

Moreover, a morphology-based tachyarrhythmia discriminator also has a weakness when the SVT rhythms exhibit a lower feature correlation coefficient. The lower feature correlation coefficient can be due to morphology changes, widened depolarization complexes, or variable block, such as rate dependent bundle branch block, or timing variation between rate and shock channels at a high ventricular rate. In certain similar circumstances, a morphology of a VT rhythm can be well-correlated to an NSR template, possibly resulting in an erroneous classification of the VT episode as an SVT episode.

Because of these limitations, the present inventors have recognized a need for improved discrimination of tachyarrhythmia. The present inventors have determined, among other things, that when a tachyarrhythmia is sudden onset and 1:1, for example, if a rate or interval-based discriminator can indicate the rhythm as a possible SVT or VT, then the specificity or sensitivity of the depolarization classification can be improved by adaptively adjusting the FCC threshold of the morphology-based discriminator.

This document discusses, among other things, systems and methods to discriminate between a ventricular tachyarrhythmia (VT) and a supraventricular tachyarrhythmia (SVT), such as upon detecting sudden onset and 1:1 tachycardia. In certain examples, a detected tachyarrhythmia is analyzed to determine whether it is sudden onset and 1:1. If so, a first fast beat is identified. One or more ventricular intervals in close proximity to the first fast beat are analyzed to determine an initial classification of either VT or SVT. The initial classification is used to adjust a morphological feature correlation coefficient (FCC) threshold. A morphology analysis is performed with the adjusted FCC threshold value to yield a secondary classification.

According to one example, there is a method for classifying a tachyarrhythmia in a heart, the method comprising sensing one or more sequences of atrial and ventricular contractions associated with the tachyarrhythmia; selecting one or more patterns of atrial and ventricular contractions; and obtaining a first classification of the tachyarrhythmia based on whether a match exists between the one or more sequences of atrial and ventricular contractions and the one or more patterns.

According to another example, there is a tachyarrhythmia detection and classification system, comprising a sensing circuit, adapted to sense at least one cardiac signal; an implant controller, coupled to the sensing circuit, the implant controller including: an arrhythmia detection module, the arrhythmia detection module adapted to detect a tachyarrhythmia based on a heart rate obtained from the at least one cardiac signal; and an arrhythmia discriminator module, the arrhythmia discriminator module adapted to create a first classification of a tachyarrhythmia as either ventricular tachycardia (VT) or supraventricular tachycardia (SVT) using one or more patterns of atrial and ventricular contractions to determine if a match exists in a sequence of atrial and ventricular depolarizations detected by the arrhythmia detection module; and a therapy circuit, coupled to the implant controller, and adapted to provide one or more therapies based on the classification.

According to another example, there is a method for characterizing a tachyarrhythmia, the method comprising sensing a tachyarrhythmia episode; capturing one or more sequences of atrial (A) and ventricular (V) contractions associated with the tachyarrhythmia episode; matching one or more patterns within the one or more sequences, wherein the one or more patterns includes an AVVA pattern, a VAAV pattern, and an AVAV pattern; characterizing the tachyarrhythmia as either more likely ventricular tachyarrhythmia (VT) or more likely supraventricular tachyarrhythmia (SVT) using at least one of the matches; establishing a morphological feature correlation coefficient threshold value depending on the characterization of the tachyarrhythmia; performing a morphology analysis using the established morphological feature correlation coefficient threshold value to obtain a VT or SVT classification; and tailoring a delivery of an anti-tachyarrhythmia therapy using the VT or SVT classification.

This summary is intended to provide an overview of certain subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present inventors have recognized, among other things, that when a tachycardia is sudden onset with a 1:1 rhythm, certain rhythm detection algorithms may fail to properly classify the tachycardia as supraventricular tachyarrhythmia (SVT) or ventricular tachyarrhythmia (VT). Furthermore, in some cases, a sinus tachycardia rhythm with a sudden rate change can be detected as sudden onset with a 1:1 rhythm and be improperly classified as VT. By analyzing the patterns of atrial and ventricular contractions in close proximity to the beginning or onset of the tachycardia, an initial classification can be made. A morphology analysis can then be performed, where the morphology analysis is customized to use information from the initial classification, such as to adaptively adjust a feature correlation coefficient (FCC) threshold value to which an FCC is compared.

Figure 1:
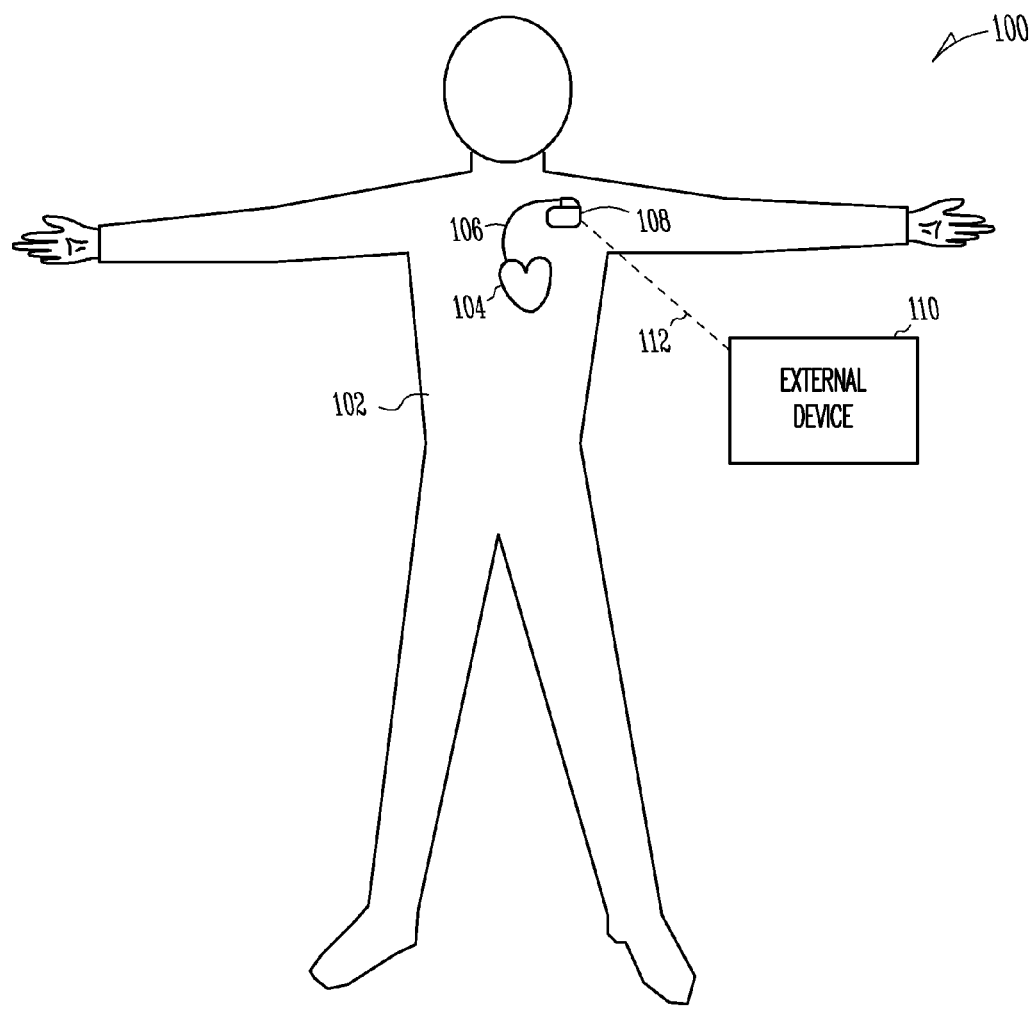
FIG. 1 is a schematic view of a system that uses an implantable medical device.

FIG. 1 illustrates an example of a system 100 that uses an implantable medical device (IMD) 108. The IMD 108 includes an electronics unit coupled by electrodes to a heart 104 of a patient 102. In the illustrated example, certain of the electrodes are disposed on an intravascular cardiac lead 106, which may include one or more leads. However, in other examples, the one or more electrodes are located at the electronics unit, and the intravascular cardiac lead 106 may be omitted. Examples of IMD 108 include, without limitation, a pacer, a defibrillator, a cardiac resynchronization therapy (CRT) device, or a combination of such devices. Typically, the system 100 also includes an external device 110 that communicates with the IMD 108 via a wireless connection 112, where the wireless connection 112 employs wireless signals such as radio frequency (RF), inductive, or other telemetry signals. In certain examples, the external device 110 is an IMD programmer module that can be used to control the IMD unit 108. In other examples, the external device 110 can include a monitoring or reporting unit optionally coupled to a computer, communications, or other network.

In an example in which the one or more intravascular cardiac leads 106 couple the IMD 108 to the heart 104, the IMD 108 is typically capable of delivering one or more therapies to the heart 104 through an electrical contact ("electrode"), which is typically in contact with an interior portion of the heart 104. Typical therapies include cardioversion, defibrillation, resynchronization, or pacing, or some combination thereof. The cardiac lead 106 or leads and electrodes may also typically be used for sensing electrical activity of the heart 104, including electrical activity related to contractions of the atria or ventricles. Alternatively, one or more electrodes at the IMD 108 can be used for sensing or delivering electrical energy, in which case the cardiac lead 106 may be omitted.

Figure 2:
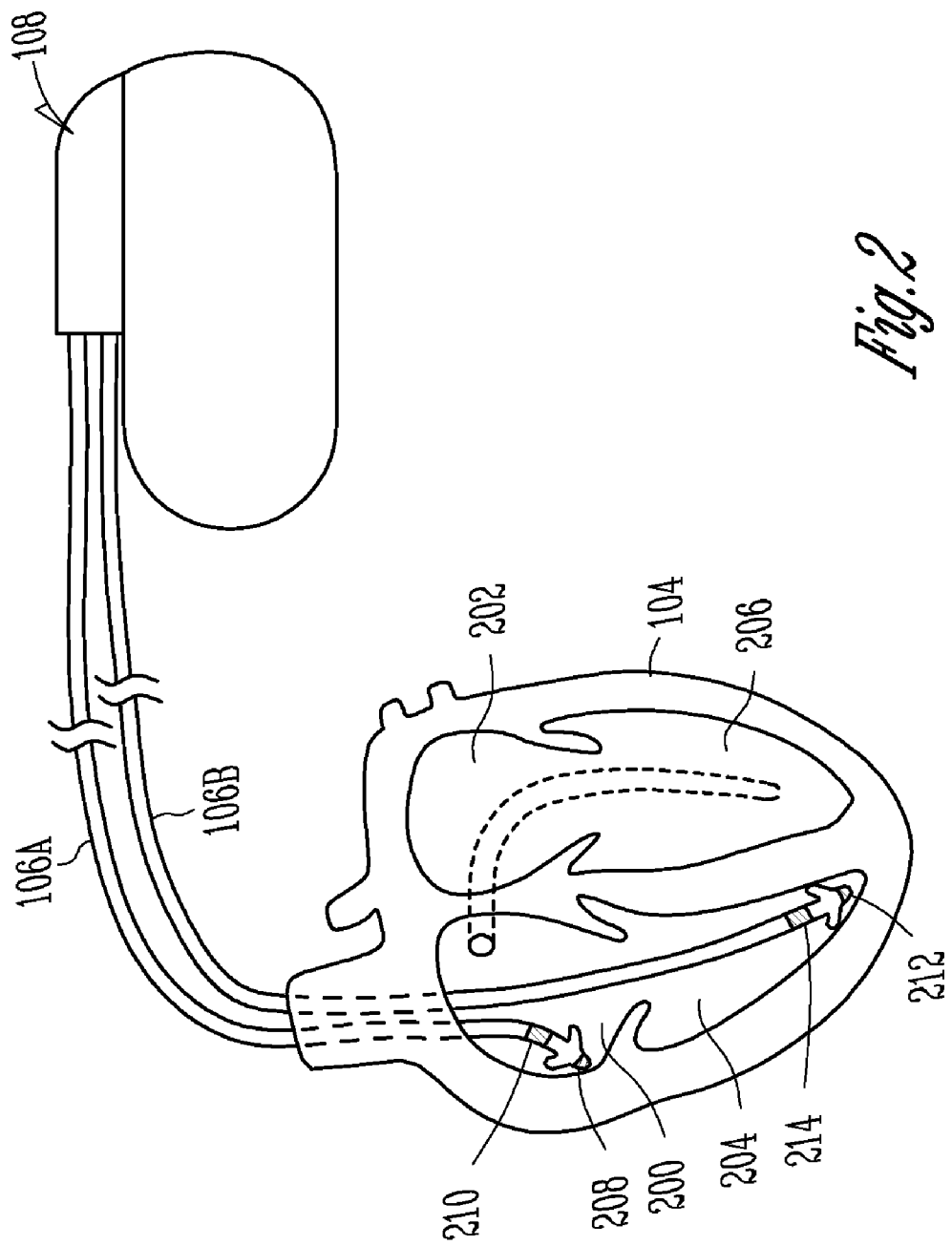
FIG. 2 is a schematic view of an exemplary implantable medical device coupled to a heart.

FIG. 2 is a schematic view of an exemplary implantable medical device 108 coupled to a heart 104. The heart 104 includes a right atrium 200, a left atrium 202, a right ventricle 204, and a left ventricle 206. In one example, the IMD unit 108 is coupled to the heart 104 with an atrial lead 106A and a ventricular lead 106B. The atrial lead 106A includes one or more electrodes, such as a tip electrode 208 and a ring electrode 210, located in the right atrium 200 for sensing signals or delivering therapy to the atrium 200. The ventricular lead 106B also includes one or more electrodes, such as a tip electrode 212 and a ring electrode 214, located in the right ventricle 204 for sensing signals or delivering therapy to the ventricle 204.

In certain examples, the ventricular lead 106B includes additional electrodes, such as to provide atrial cardioversion, atrial defibrillation, ventricular cardioversion, ventricular defibrillation, or combinations thereof to the heart 104. Such cardioversion or defibrillation electrodes typically have larger surface areas than pacing electrodes to handle the higher energies involved in defibrillation. In other examples, the ventricular lead 106B provides resynchronization therapy to the heart 104. Other forms of electrodes include meshes and patches which may be applied to portions of the heart 104 or which may be implanted in other areas of the body to sense electrical signals or to help "steer" electrical currents produced by IMD 108. The present methods and systems will work in a variety of configurations and with a variety of electrodes.

Figure 3:
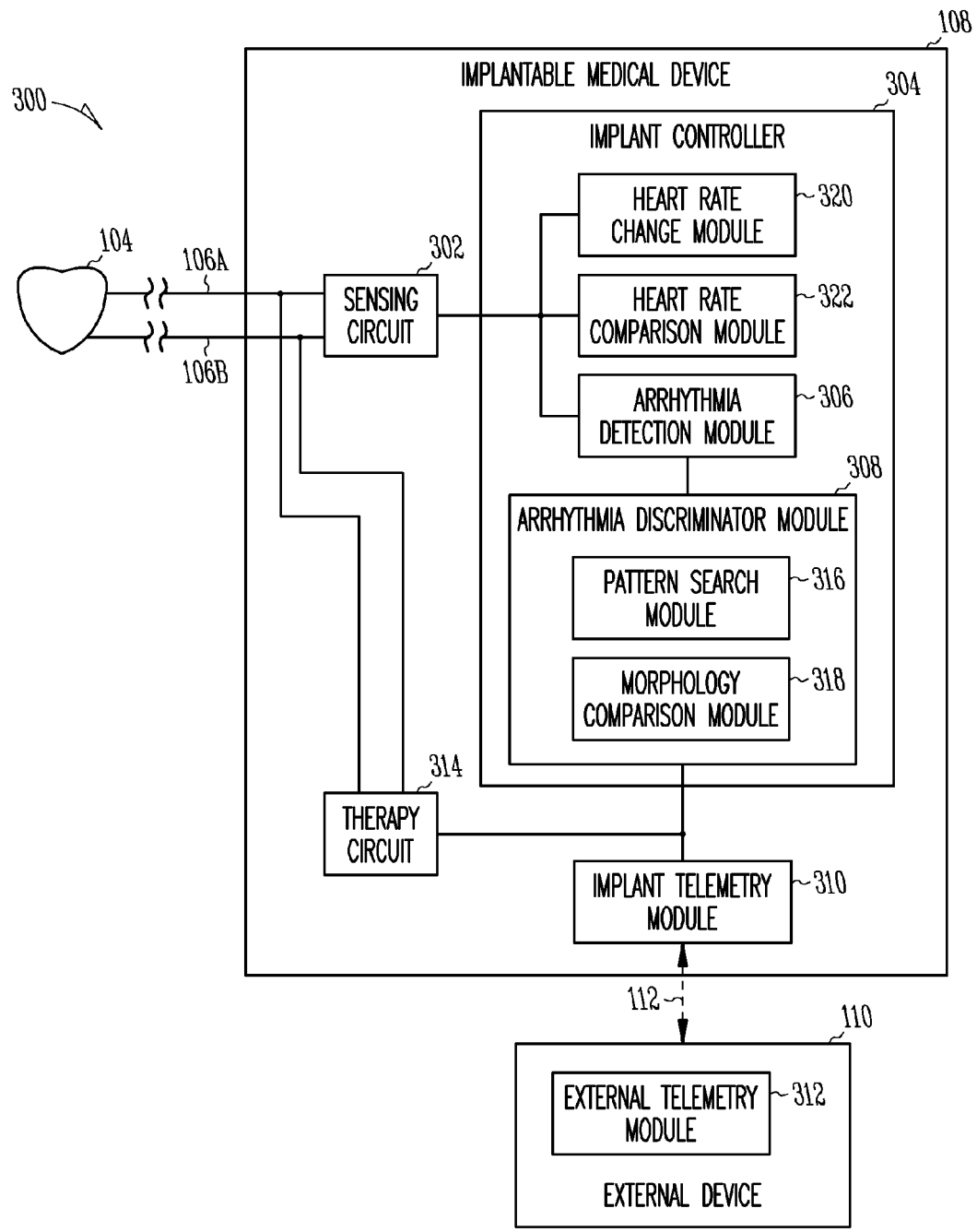
FIG. 3 is a schematic view of a system that detects and discriminates tachyarrhythmia.

FIG. 3 is a schematic view of a system 300 that detects and classifies or discriminates between tachyarrhythmias. In this example, a sensing circuit 302 is connected to the heart 104 by one or more electrodes, such as by using an atrial lead 106A and a ventricular lead 106B. The sensing circuit 302 provides sensed atrial and ventricular signals to the implant controller circuit 304. In some examples, a heart rate change module 320 uses the signals provided by the sensing circuit 302 to determine if the tachyarrhythmia is sudden onset. Additionally, in other examples, a heart rate comparison module 322 uses the signals provided by the sensing circuit 302 to determine if the tachyarrhythmia has a 1:1 atrial-to-ventricular rate. In the controller 304, an arrhythmia detection module 306 uses the signals provided by the sensing circuit 302 to detect an arrhythmia, and an arrhythmia discrimination module 308 classifies the arrhythmia as either ventricular (VT) or supraventricular (SVT) in origin by performing searches for certain patterns of atrial and ventricular signals using the pattern search module 316. In some examples, after an initial classification is found by the pattern search module 316, a secondary classification is determined by the morphology comparison module 318. A therapy circuit 314 uses the results from the implant controller 304 to provide pacing, defibrillation, or one or more other therapies to the heart 104, such as by using the one or more leads 106A, 106B. The implant controller 304 communicates with the implant telemetry module 310. The implant telemetry module 310 sends and receives information via an inductive, radio frequency, or other wireless connection 112 to an external device 110. In some examples, a local or remote caregiver or other user can use the external device 110 to interact with or control the implant controller 304, for example, by reprogramming the controller 304 with upgraded or different methods or algorithms or control parameters. In other examples, the external device 110 receives information through the external telemetry module 312 to generate reports, real-time statistics, or other information for the local or remote caregiver or other user.

Figure 4:
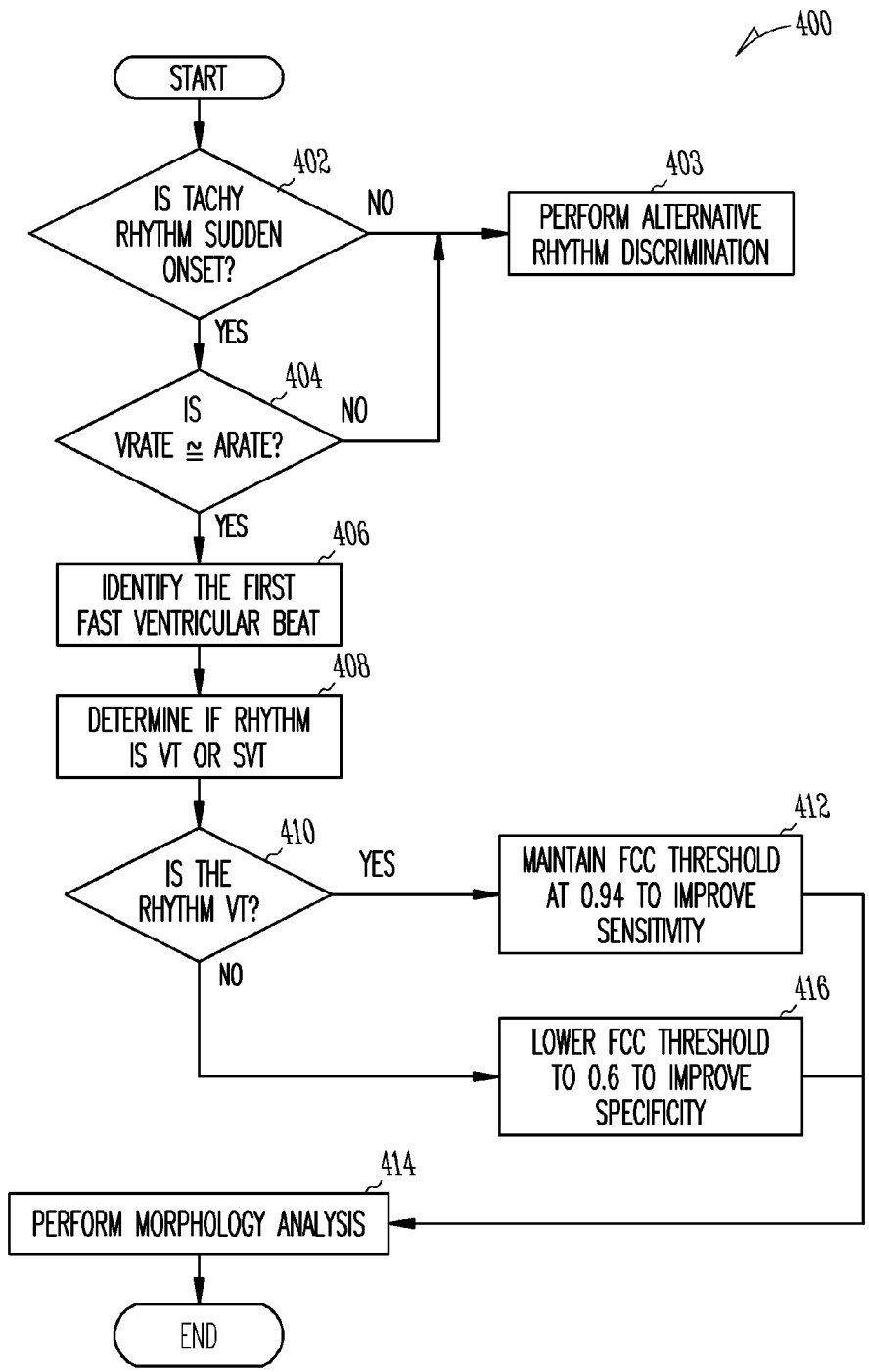
FIG. 4 is a flowchart illustrating generally the process of detecting and discriminating tachyarrhythmia.

FIG. 4 is a flowchart illustrating an example of a method 400 for detecting and classifying or discriminating between tachyarrhythmias. At 402, a signal indicating a tachyarrhythmia is received and analyzed to determine if the tachyarrhythmia exhibits a sudden onset. In one example, the sudden onset determination is performed by first detecting multiple fast beats, where a fast beat rate is 10% or faster than an average beat rate. When more than two consecutive fast beats are detected, the rhythm is considered sudden onset. Such analysis can be performed on either the atrial or ventricular rhythm. If the signal is not found to be sudden onset, then at 403, other rhythm discrimination methods may be implemented.

At 404, if the tachyarrhythmia is determined to be sudden onset, then the ventricular rate is compared to the atrial rate to find if they are substantially equal, that is, a 1:1 atrial-to-ventricular rate. In an illustrative example, if the atrial rate is within 20 bpm of the ventricular rate, then the rates are deemed substantially equal. If the atrial and ventricular rates are not substantially equal, then at 403, other rhythm discrimination methods may be implemented.

At 406, if the tachyarrhythmia episode exhibits a sudden onset with a 1:1 relationship between atrial and ventricular rate, then the atrial and ventricular beats associated with the tachyarrhythmia episode are examined for the first "fast" ventricular beat of the tachyarrhythmia, which is the beginning of the sudden onset pattern. In one example, the pattern of more than two consecutive fast beats, which was detected during at 402, is analyzed and the first beat in the sequence is identified. In another example, a zoneless tachy detection method, as described in "ZONELESS TACHYARRHYTHMIA DETECTION WITH REAL-TIME RHYTHM MONITORING," application Ser. No. 11/301,716, filed on Dec. 13, 2005, is used to detect the series of fast beats. In yet another example, a series of fast beats is detected using hysteresis, as described in "TACHYARRHYTHMIA SUDDEN ONSET DETECTION WITH HYSTERESIS," application Ser. No. 11/301,440, filed on Dec. 13, 2005.

At 408, the sudden onset pattern is analyzed to provide an initial determination of whether the tachyarrhythmia is SVT or VT. This can be accomplished using several methods, as described below. The initial classification can be used either independently or in conjunction with further classifications to refine or substantiate the initial classification.

Figure 5:
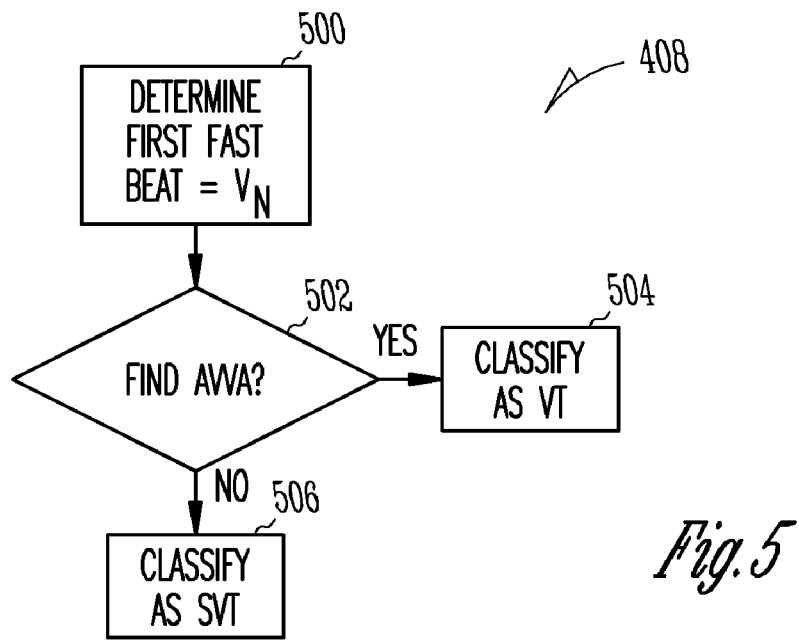
FIG. 5 is a flowchart illustrating generally one example of discriminating a tachyarrhythmia.

FIG. 5 is a flowchart illustrating one example of a method 408 of classifying a sudden onset 1:1 tachyarrhythmia as VT or SVT. At 500, a first fast ventricular beat is identified and saved as $V_n$. At 502, sequences of ventricular and atrial beats associated with the tachyarrhythmia are analyzed. In one example, the analysis begins at some number of ventricular beats before the identified first fast ventricular beat $V_n$, for example, three beats before. Other examples may analyze the sequence of atrial and ventricular beats beginning with a ventricular beat that occurs earlier or later. In this example, beginning at the third ventricular beat before the first fast ventricular beat, labeled $V_{n-3}$ in FIG. 5, if two ventricular beats (which can be labeled on a timing diagram as a "V" event) are between two consecutive atrial beats (which can be labeled "A" events on a timing diagram), such that the temporal sequence AVVA is formed, then, at 504, the tachyarrhythmia is classified as VT (or, alternatively, as more likely to be VT). Alternatively, if the particular sequence of atrial and ventricular beats is not found, then at 506, the tachyarrhythmia is classified as SVT (or, alternatively, as more likely to be SVT).

Figure 9:
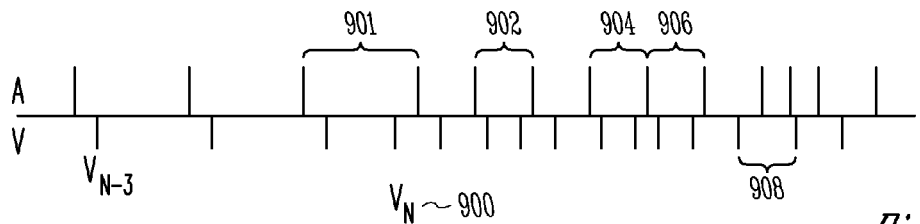
FIG. 9 is a timing diagram illustrating a sequence of atrial and ventricular contractions.

FIG. 9 is a timing diagram illustrating a sequence of atrial and ventricular contractions. In accordance with the method 408 as illustrated in FIG. 5, a first fast ventricular beat 900 is identified and saved as $V_n$. In one example, starting at a defined number of beats (e.g., three) before the first fast ventricular beat 900, the sequence is searched for the patterns of AVVA. In this example, the pattern AVVA 901, 902, 904, 906 occurs four times after $V_{n-3}$. In addition, the pattern VAAV 908 occurs once. Using the method 408 as shown in detail in FIG. 5, this sequence would be classified as VT, or VT-likely. It should be noted that if there are too many intervals of AVVA, then typically, the number of ventricular beats are much greater than the number of atrial beats such that the arrhythmia can no longer be properly classified as 1:1.

Figure 6:
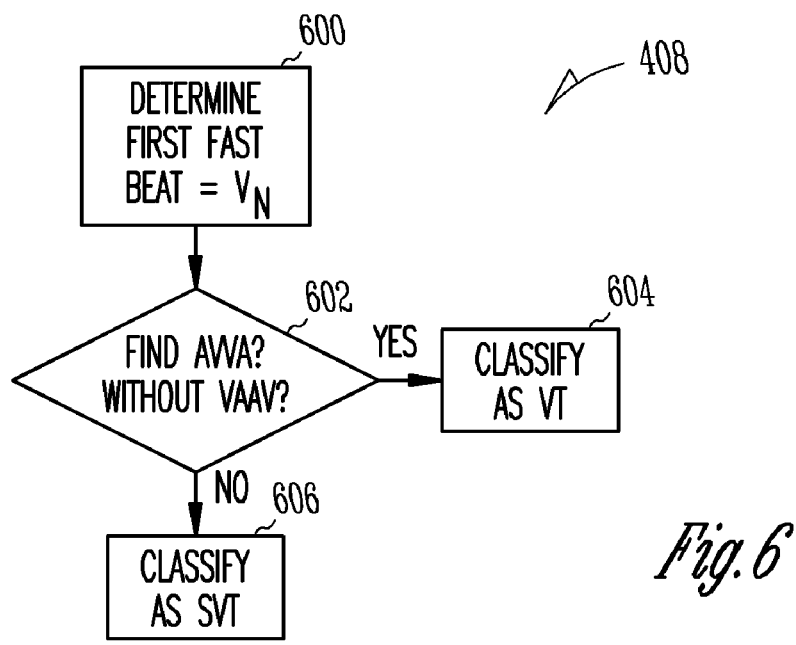
FIG. 6 is a flowchart illustrating generally another example of discriminating a tachyarrhythmia.

FIG. 6 is a flowchart illustrating another example of a method 408 of classifying a sudden onset 1:1 tachyarrhythmia. At 600, a first fast ventricular beat is identified and saved as $V_n$. At 602, sequences of ventricular and atrial beats associated with the tachyarrhythmia are analyzed. Again, analysis could begin at any ventricular beat before or after the first fast ventricular beat. In one example, beginning at the third ventricular beat before the first fast ventricular beat, if any of the following two ventricular beats are between two consecutive atrial beats, such that the temporal sequence AVVA is formed, without the pattern of two atrial beats between two consecutive ventricular beats (VAAV) occurring, then, at 604, the tachyarrhythmia is classified as VT (or, alternatively, as more likely to be VT). Alternatively, if the particular sequence of atrial and ventricular beats is not found, then at 606, the tachyarrhythmia is classified as SVT (or, alternatively, as more likely to be SVT).

Figure 10:
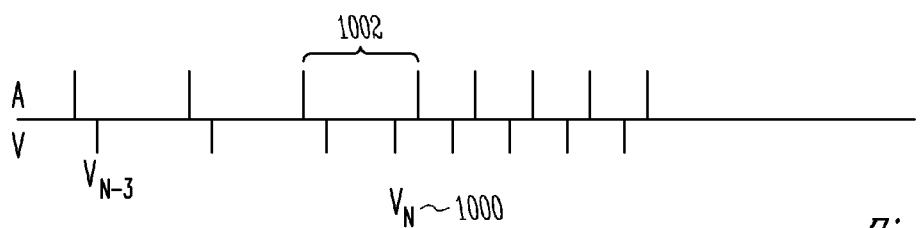
FIG. 10 is a timing diagram illustrating a sequence of atrial and ventricular contractions.

FIG. 10 is a timing diagram illustrating a sequence of atrial and ventricular contractions. In accordance with the method 408 as illustrated in FIG. 6, a first fast ventricular beat 1000 is identified and saved as $V_n$. In this example, starting at the third ventricular beat before the first fast ventricular beat 1000, the sequence of atrial and ventricular beats is searched for the patterns of AVVA and VAAV. As illustrated, the pattern AVVA 1002 occurs once and there are no occurrences of the pattern VAAV (a pattern that typically indicates that ventricular tachycardia is more likely). Thereafter, the atrial and ventricular contractions exhibit a steady-state 1:1 rhythm. Using the method 408 as shown in detail in FIG. 6, this sequence would be classified as VT, or VT-likely.

In certain examples, the search for the one or more patterns is bounded. This could be implemented by using a range of atrial or ventricular beats, using a maximum time threshold, or by other methods to limit the search space to an interval around an identified sudden onset pattern. Two examples are provided and described below.

Figure 7:
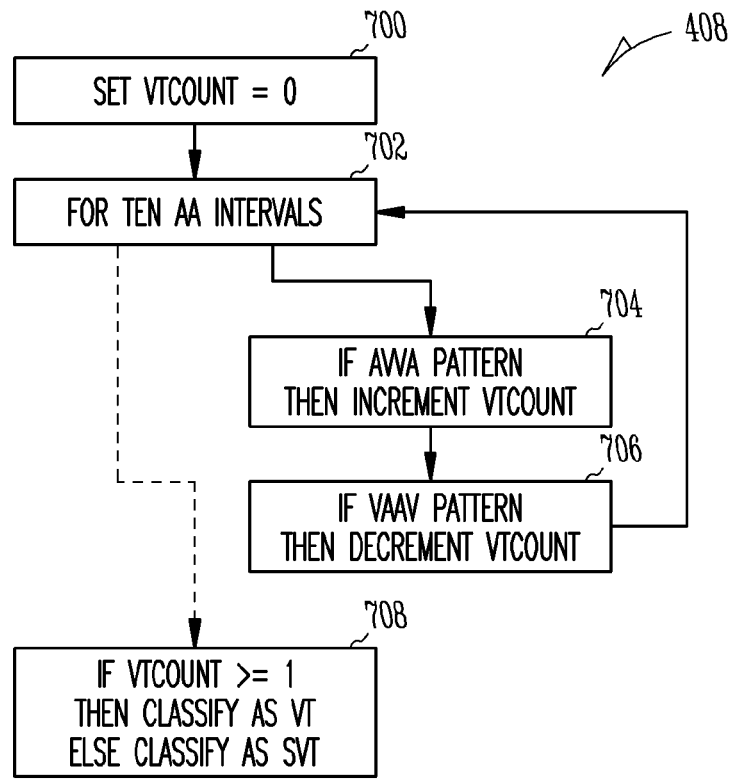
FIG. 7 is a flowchart illustrating generally another example of discriminating a tachyarrhythmia.

FIG. 7 is a flowchart illustrating another example of a method 408 of classifying a sudden onset 1:1 tachyarrhythmia. Typically, a fast ventricular rate is associated with VT, thus, when analyzing a range of ventricular and atrial beats, if consecutive sequences of ventricular beats are found (without an intervening atrial beat), then it may be an indication of ventricular tachyarrhythmia. In the example of FIG. 7, at 700, a counter variable VTCount is initialized to zero. At 702, for a given number (e.g., ten) of atrial intervals between pairs of successive atrial beats, the counter variable VTCount is incremented or decremented depending on the patterns of atrial and ventricular beats found. In one example, the first atrial interval is arranged around the first fast ventricular beat. In other examples, the first atrial interval is at some position before or after the first fast ventricular beat. At 704, if the pattern of two ventricular beats occurring between two consecutive atrial beats (AVVA) is found, then the counter variable VTCount is incremented (thereby increasing the likelihood of classifying the tachyarrhythmia VT, or inversely, decreasing the likelihood of classifying the tachyarrhythmia as SVT). At 706, if the pattern of two atrial beats occurring between two consecutive ventricular beats (VAAV) is found, then the counter variable VTCount is decremented (thereby decreasing the likelihood of classifying the tachyarrhythmia as VT, or inversely, increasing the likelihood of classifying the tachyarrhythmia as SVT). At 708, after the given number of atrial intervals has been analyzed, the counter variable is evaluated. If VTCount is greater than or equal to a given threshold value (e.g., one), then the tachyarrhythmia is classified as VT. Otherwise, the tachyarrhythmia is classified as SVT.

Figure 11:
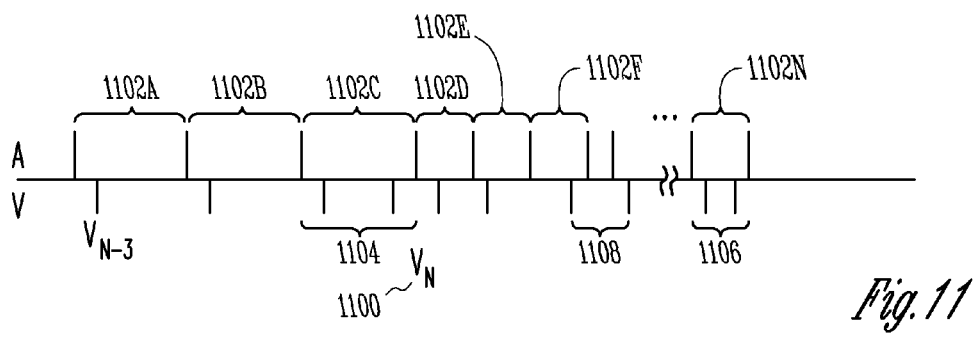
FIG. 11 is a timing diagram illustrating a sequence of atrial and ventricular contractions.

FIG. 11 is a timing diagram illustrating a sequence of atrial and ventricular contractions. In accordance with the method 408 as illustrated in FIG. 7, a first fast ventricular beat 1100 is identified and saved as $V_n$. In one example, the first atrial interval 1102A is positioned at the atrial beat immediately before the third ventricular beat before the first fast ventricular beat 1100. A given number of atrial intervals 1102A, 1102B, 1102C, . . . , 1102N are searched for the patterns AVVA and VAAV. In this example, the pattern AVVA 1104, 1106 occurs twice. In addition, the pattern VAAV 1108 is found once. Using the method 408 as shown in FIG. 7, the counter value would be incremented twice and decremented once, resulting in a final value of one (assuming that the counter value was initialized to zero). In this example, this sequence would be classified as VT, or VT-likely, because the counter value met or exceeded the threshold (e.g., one).

Figure 8:
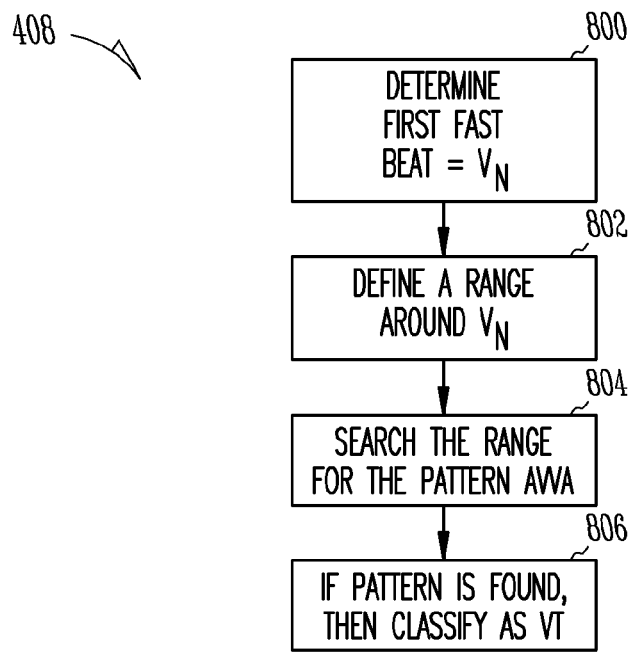
FIG. 8 is a flowchart illustrating generally another example of discriminating a tachyarrhythmia.

FIG. 8 is a flowchart illustrating another example of a method 408 of discriminating a sudden onset 1:1 tachyarrhythmia. At 800, the first fast ventricular beat associated with the tachyarrhythmia is identified and saved as $V_n$. At 802, a range of ventricular intervals is defined. In one example, the range is defined to be the consecutive beats between $V_{n-3}$ to $V_{n+1}$, which would include the ventricular intervals $[V_{n-3}, V_{n-2}], [V_{n-2}, V_{n-1}], \ldots, [V_n, V_{n+1}]$. At 804, the range of ventricular beats between $V_{n-3}$ to $V_{n+1}$ is searched for the pattern AVVA, where A indicates an atrial beat and V indicates a ventricular beat. At 806, if the pattern AVVA is found in the range, then the tachyarrhythmia is classified as VT (or, alternatively, as more likely VT, such as in an implementation where a counter VTCount is used, such as discussed above).

Figure 12:
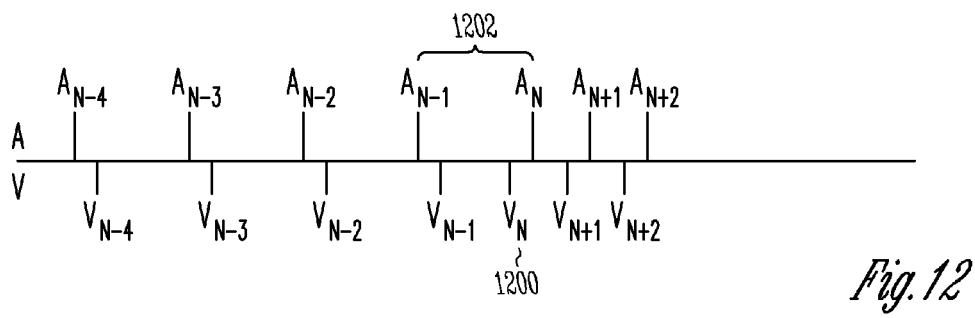
FIG. 12 is a timing diagram illustrating a sequence of atrial and ventricular contractions.

FIG. 12 is a timing diagram illustrating a sequence of atrial and ventricular contractions. In accordance with the method 408 as illustrated in FIG. 8, a first fast ventricular beat 1200 is identified and saved as $V_n$. A range is defined around the first fast beat $V_n$. In this example, the range is defined to be the consecutive beats between $V_{n-3}$ to $V_{n+1}$, which would include the ventricular intervals $[V_{n-3}, V_{n-2}], [V_{n-2}, V_{n-1}], \ldots, [V_n, V_{n+1}]$. This range is searched for the pattern AVVA. In this example, the pattern AVVA 1202 occurs once. Using the method 408 as shown in detail in FIG. 8, because the pattern AVVA was found in the range, this sequence would be classified as VT, or VT-likely. In other examples, the range can be extended to include more beats before or after the first fast beat $V_n$. For example, the range could be defined to be the consecutive beats between $V_{n-4}$ to $V_{n+2}$.

In certain examples, alternative search patterns that include two or more ventricular beats occurring between two consecutive atrial beats, such as AVVVA, can be used, either individually or in combination with other patterns (e.g., AVVA), to indicate that a tachyarrhythmia is more likely VT. Similarly, patterns that include two or more atrial beats occurring between two consecutive ventricular beats, such as VAAAV, are indicative that a tachyarrhythmia is more likely SVT in origin, and can be used in analogous methods.

At 410, the initial VT/SVT classification is evaluated. If the tachyarrhythmia is initially classified as VT, then at 412, a value of a feature correlation coefficient (FCC) is maintained at a relatively large value (e.g., 0.94) to improve the sensitivity of morphology-based VT classification. In general, a morphology analysis compares the ventricular beat morphology to a template. The FCC, which indicates a degree of similarity between the morphology of the beat under examination and the morphology of the template beat, is compared to an FCC threshold value. The FCC can be thought of as a matching value, where a perfect match between the morphology of the beat under examination and a morphology of the template beat will result in an FCC=1.0. Enforcing a higher matching threshold (FCC threshold) may result in better sensitivity. Sensitivity generally refers to the ability of the detection scheme to effectively detect a particular abnormal heart rhythm, for example, VT. Sensitivity can be expressed with the formula: sensitivity=(true positives)/(true positives+false negatives). Thus, a higher sensitivity generally indicates that an analysis correctly characterizes more true positives or eliminates false negatives.

In this example, the initial interval-based classification of VT provides at least some evidence that the tachyarrhythmia is a VT. Thus, to overcome the initial classification as a VT with a conflicting morphology analysis, a high correlation must be found between the morphology of the beat under examination and the morphology of a template indicative of an SVT or NSR rhythm. In certain examples, the FCC threshold is maintained at its initial value (e.g., 0.94) in response to the initial VT classification. This reduces the likelihood that the morphology-based classification will classify the heart beat under examination as an SVT beat, thereby improving the sensitivity of VT detection.

At 416, if the tachyarrhythmia is initially classified as SVT, then the FCC threshold value is adaptively lowered in response to the initial classification as SVT. In certain examples, a low threshold is initially established and if the initial classification is SVT, then the threshold is maintained. In either case, the lowered threshold improves the specificity of classifying a tachyarrhythmia as VT because it makes it more likely that the morphology analysis will result in an SVT classification. Specificity generally refers to the ability of the detection scheme to avoid improper classifications. Specificity can be expressed with the function: specificity=(true negatives)/(true negatives+false positives). Thus, a higher specificity generally reflects more accurate classification of true negatives or reduction of false positives. In one example, the FCC threshold is adaptively lowered to 0.6 from an initial value (e.g., 0.94) to improve the specificity of classifying the arrhythmia as VT. By reducing the FCC threshold, there is an increased likelihood that the morphology analysis will classify the arrhythmia as SVT, which directly corresponds to a decreased likelihood that the arrhythmia will be classified as VT. Thus, in the event that the arrhythmia is classified as VT by the morphology analysis, there is an increased chance that it is not a false positive, and thereby, the specificity is increased.

After the FCC threshold value has been adjusted, at 414, a morphology analysis is performed. This yields a secondary tachyarrhythmia classification as VT or SVT. This secondary tachyarrhythmia classification (which has been influenced by the initial tachyarrhythmia classification) can then be used in an algorithm that controls evaluation and delivery of appropriate anti-tachyarrhythmia therapy. Appropriate therapies may include pacing, shock, or no therapy depending on the a priori knowledge of the patient and the current classification. In one example, as described in commonly assigned Kim et al. U.S. Pat. No. 6,708,058 entitled "NORMAL CARDIAC RHYTHM TEMPLATE GENERATION SYSTEM AND METHOD," issued on Mar. 16, 2004, which is incorporated by reference herein in its entirety, the morphology analysis determines if eight or more beats out of ten beats are uncorrelated and if so, then the rhythm is classified as VT.

In certain examples, a morphology-based classification of the tachyarrhythmia is weighted and compared to the initial classification to determine a final accepted classification. For example, one or both of the first and second classifications could be represented using a continuous metric, which could then be mathematically combined to determine a weighted probability of a particular type of arrhythmia. In another example, the first and second classifications could be assigned a particular weight or confidence level that represents an inherent or evaluated accuracy of a classification methodology. In yet another example, a constant or other factor could be used in the secondary classification (e.g., a morphology) to bias or weigh the correspondence value (e.g., a feature correlation coefficient). Optionally, the secondary classification can be obtained using other tachyarrhythmia discrimination methods, such as a rate or interval-based method, e.g., Stability.

While this document discusses searching for patterns of atrial and ventricular beats in an attempt to initially classify an arrhythmia as VT, it should be noted that a complementary system could be implemented such that the initial classification would be SVT and an appropriate complementary morphology analysis (e.g., using one or more VT templates) is used to determine whether SVT is exhibited.

The accompanying drawings that form a part hereof, show by way of illustration, and not of limitation, specific examples in which the subject matter may be practiced. The examples illustrated are described in sufficient detail to enable those skilled in the art to practice the teachings disclosed herein. Other examples may be utilized and derived therefrom, such that structural and logical substitutions and changes may be made without departing from the scope of this disclosure. This Detailed Description, therefore, is not to be taken in a limiting sense, and the scope of various examples is defined only by the appended claims, along with the full range of equivalents to which such claims are entitled. For example, the pattern matching-based tachyarrhythmia classification can be combined with other methods of tachyarrhythmia classification to enhance the accuracy of classification of 1:1 tachyarrhythmias.

Such examples of the inventive subject matter may be referred to herein, individually and/or collectively, by the term "invention" merely for convenience and without intending to voluntarily limit the scope of this application to any single invention or inventive concept if more than one is in fact disclosed. Thus, although specific examples have been illustrated and described herein, it should be appreciated that any arrangement calculated to achieve the same purpose may be substituted for the specific examples shown. This disclosure is intended to cover any and all adaptations, or variations, or combinations of various examples. Combinations of the above examples, and other examples not specifically described herein, will be apparent to those of skill in the art upon reviewing the above description.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A tachyarrhythmia detection and classification system, comprising:
    a sensing circuit to sense at least one cardiac signal; and
    an implant controller, coupled to the sensing circuit, the implant controller including:
        an arrhythmia discriminator module, the arrhythmia discriminator module to create a first classification of a tachyarrhythmia as either ventricular tachycardia (VT) or supraventricular tachycardia (SVT) and to discriminate between VT and SVT using one or more template patterns of respective sequences of atrial and ventricular contractions to determine how many template patterns occur in a sequence of detected atrial and ventricular depolarizations, wherein to determine how many template patterns occur in the sequence of atrial and ventricular depolarizations, the arrhythmia discriminator module is to:
        count a number of one or more VT-likely template patterns representing one or more corresponding indications that a ventricular tachyarrhythmia is likely; and
        characterize the first classification of the tachyarrhythmia as more likely indicative of ventricular tachycardia if the number of one or more VT-likely template patterns representing one or more corresponding indications that a ventricular tachyarrhythmia is likely exceeds a threshold number.

2. The system of claim 1, wherein to determine how many template patterns occur in the sequence of atrial and ventricular depolarizations, the arrhythmia discriminator module is to:
    count a number of one or more SVT-likely template patterns representing one or more corresponding indications that a supraventricular tachyarrhythmia is likely; and
    characterize the first classification of the tachyarrhythmia as more likely indicative of supraventricular tachycardia if the number of one or more SVT-likely template patterns representing one or more corresponding indications that a supraventricular tachyarrhythmia is likely exceeds a threshold number.

3. The system of claim 1, comprising an arrhythmia detection module, coupled to the implant controller, and to detect the tachyarrhythmia based on a heart rate obtained from the at least one cardiac signal.

4. The system of claim 1, comprising a heart rate change module, coupled to the implant controller, and to detect a sudden onset of a tachyarrhythmia.

5. The system of claim 1, comprising a heart rate comparison module, coupled to the implant controller, and to detect whether the atrial rate is substantially equal to a ventricular rate.

6. The system of claim 1, wherein the arrhythmia discriminator module comprises:
    a pattern of two or more ventricular contractions occurring between consecutive atrial contractions; and
    a pattern search module to classify the sequence of atrial and ventricular depolarizations as more likely indicative of ventricular tachyarrhythmia if the first pattern is found in the sequence of atrial and ventricular depolarizations.

7. The system of claim 1, wherein the arrhythmia discriminator module comprises:
    a pattern of two or more atrial contractions occurring between consecutive ventricular contractions; and
    a pattern search module to classify the sequence of atrial and ventricular depolarizations as more likely indicative of supraventricular tachyarrhythmia if the second pattern is found in the sequence of atrial and ventricular depolarizations.

8. The system of claim 1, wherein the arrhythmia discriminator module comprises:
    a first pattern of two or more ventricular contractions occurring between consecutive atrial contractions;
    a second pattern of two or more atrial contractions occurring between consecutive ventricular contractions; and
    a pattern search module to classify the sequence of atrial and ventricular depolarizations as more likely indicative of ventricular tachyarrhythmia if the first pattern is found in the sequence of atrial and ventricular depolarizations without finding the second pattern.

9. The system of claim 1, wherein the arrhythmia discriminator module comprises:
    one or more VT-likely patterns indicative of a likelihood of ventricular tachyarrhythmia;
    one or more SVT-likely patterns indicative of a likelihood of SVT;
    a counter initialized to a counter value at the onset of a tachyarrhythmia episode, wherein the counter is incremented for each VT-likely pattern found in the sequence of atrial and ventricular depolarizations and the counter is decremented for each SVT-likely pattern found in the sequence of atrial and ventricular depolarizations; and
    a pattern search module to classify the sequence of atrial and ventricular depolarizations as more likely indicative of ventricular tachyarrhythmia if the counter value exceeds a threshold value.

10. The system of claim 1, wherein the arrhythmia discriminator module comprises:
    a matching threshold value established based on the first classification; and
    a morphology comparison module to compare a morphology of one or more beats to a template morphology using the matching threshold value to obtain a second classification of the tachyarrhythmia.

11. The system of claim 1, comprising a therapy circuit, coupled to the implant controller, and to provide one or more therapies based on how many template patterns occur in the sequence of atrial and ventricular depolarizations.

12. A method comprising:
  detecting a tachyarrhythmia in a sequence of atrial and ventricular depolarizations; and
  creating a first classification of a tachyarrhythmia as either ventricular tachycardia (VT) or supraventricular tachycardia (SVT) and to discriminate between VT and SVT using one or more template patterns of respective sequences of atrial and ventricular contractions to determine how many template patterns occur in the sequence of detected atrial and ventricular depolarizations, wherein to determine how many template patterns occur in the sequence of atrial and ventricular depolarizations, the method comprises:
    counting a number of one or more VT-likely template patterns representing one or more corresponding indications that a ventricular tachyarrhythmia is likely; and
    characterizing the first classification of the tachyarrhythmia as more likely indicative of ventricular tachycardia if the number of one or more VT-likely template patterns representing one or more corresponding indications that a ventricular tachyarrhythmia is likely exceeds the threshold number.

13. The method of claim 12, wherein to determine how many template patterns occur in the sequence of atrial and ventricular depolarizations, the method comprises:
  counting a number of one or more SVT-likely template patterns representing one or more corresponding indications that a supraventricular tachyarrhythmia is likely; and
  characterizing the first classification of the tachyarrhythmia as more likely indicative of supraventricular tachycardia if the number of one or more SVT-likely template patterns representing one or more corresponding indications that a supraventricular tachyarrhythmia is likely exceeds the threshold number.

14. The method of claim 12, comprising providing one or more therapies based on how many template patterns occur in the sequence of atrial and ventricular depolarizations.

15. A non-transitory machine-readable medium comprising instructions, which when executed by a machine, cause the machine to:
  detect a tachyarrhythmia in a sequence of atrial and ventricular depolarizations; and
  create a first classification of a tachyarrhythmia as either ventricular tachycardia (VT) or supraventricular tachycardia (SVT) and to discriminate between VT and SVT using one or more template patterns of respective sequences of atrial and ventricular contractions to determine how many template patterns occur in the sequence of detected atrial and ventricular depolarizations by counting a number of one or more VT-likely template patterns representing one or more corresponding indications that a ventricular tachyarrhythmia is likely, and characterizing the first classification of the tachyarrhythmia as more likely indicative of ventricular tachycardia if the number of one or more VT-likely template patterns representing one or more corresponding indications that a ventricular tachyarrhythmia is likely exceeds a threshold number.

16. The machine-readable medium of claim 15, wherein the instructions to determine how many template patterns occur in the sequence of atrial and ventricular depolarizations, comprise instructions, which when executed by the machine, cause the machine to:
  counting a number of one or more SVT-likely template patterns representing one or more corresponding indications that a supraventricular tachyarrhythmia is likely; and
  characterizing the first classification of the tachyarrhythmia as more likely indicative of supraventricular tachycardia if the number of one or more SVT-likely template patterns representing one or more corresponding indications that a supraventricular tachyarrhythmia is likely exceeds a threshold number.

* * * * *